United States Patent [19]

Galibert et al.

[11] 4,428,941

[45] Jan. 31, 1984

[54] NUCLEOTIDIC SEQUENCE CODING THE SURFACE ANTIGEN OF THE HEPATITIS B VIRUS, VECTOR CONTAINING SAID NUCLEOTIDIC SEQUENCE, PROCESS ALLOWING THE OBTENTION THEREOF AND ANTIGEN OBTAINED THEREBY

[75] Inventors: Francis Galibert, Saint-Gratien; Pierre Tiollais, Paris; Patrick Charnay, Boulogne-Billancourt, all of France

[73] Assignees: Institut Pasteur; Institut National de la Sante et de la Recherche Medicale, both of Paris, France

[21] Appl. No.: 261,199

[22] PCT Filed: Aug. 29, 1980

[86] PCT No.: PCT/FR80/00133

§ 371 Date: Apr. 30, 1981

§ 102(e) Date: Apr. 29, 1981

[87] PCT Pub. No.: WO81/00577

PCT Pub. Date: Mar. 5, 1981

[30] Foreign Application Priority Data

Aug. 3, 1979 [FR] France .............................. 79 21811
Apr. 22, 1980 [FR] France .............................. 80 09039

[51] Int. Cl.³ .................... C07C 103/52; A61K 37/02
[52] U.S. Cl. .............................. 424/177; 260/112.5 R

[58] Field of Search .................. 260/112.5 R; 424/177

[56] References Cited

PUBLICATIONS

Murray et al., "European Patent Application", 13828, Aug. 6, 1980.
Galibert et al., Nature, 281, 646–650 (1979).
Pasek et al., Nature, 282, 575–579 (1979).
Valenzuela et al., Nature, 280, 815–819 (1979).
Charnay et al., Nature, 286, 893–895 (1980).
Sninsky et al., Nature, 279, 346–348 (1979).
Burrell et al., Nature, 279, 43–47 (1979).

*Primary Examiner*—Delbert R. Phillips
*Assistant Examiner*—F. T. Moezie
*Attorney, Agent, or Firm*—Weiser & Stapler

[57] ABSTRACT

Nucleic acid of reduced size and vector containing said nucleotidic sequence of which DNA codes an immunogenic peptidic sequence capable of inducing the generation of antibodies to the virus of viral hepatitis B. It comprises totally or partly the sequence of nucleotides represented in FIG. 3A. Application to the production by cloning in a bacterium of an immunogenic protein immunizing against hepatitis B, or application to the obtention of probes for the diagnosis of the presence of Dane particles in a serum.

10 Claims, 18 Drawing Figures

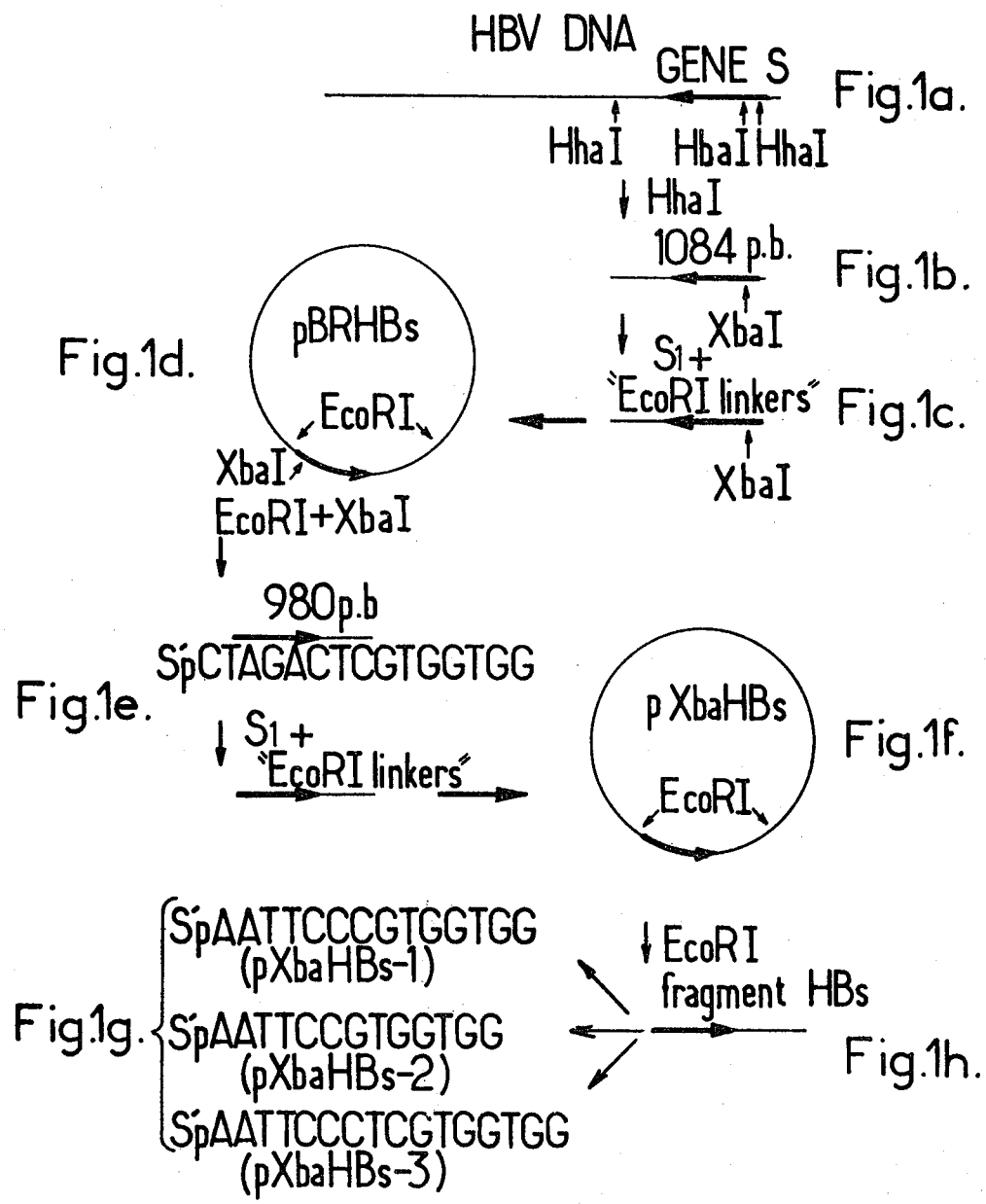

Fig.2A.

```
                    AvaIII(2116)         HhaI(1952)      HincII(2191)

1930        1940         1950         1960         1970         1980
    TCGGCAGAGG   AGCCGAAAAG   GTTCCACGCA   TGCGCTGATG   GCCCATGACC   AAGCCCCAGC
    AGCCGTCTCC   TCGGCTTTTC   CAAGGTGCGT   ACGCGACTAC   CGGGTACTGG   TTCGGGGTCG
       1990        2000         2010         2020         2030         2040
    CAGTGGGGGT   TGCGTCAGCA   AACACTTGGC   ACAGACCTGG   CCGTTGCCGG   GCAACGGGGT
    GTCACCCCCA   ACGCAGTCGT   TTGTGAACCG   TGTCTGGACC   GGCAACGGCC   CGTTGCCCCA
       2050        2060         2070         2080         2090         2100
    AAAGGTTCAG   GTATTGTTTA   CACAGAAAGG   CCTTGTAAGT   TGGCGAGAAA   GTGAAAGCCT
    TTTCCAAGTC   CATAACAAAT   GTGTCTTTCC   GGAACATTCA   ACCGCTCTTT   CACTTTCGGA
       2110        2120         2130         2140         2150         2160
    GCTTAGATTG   AATACATGCA   TACAAAGGCA   TCAACGCAGG   ATAACCACAT   TGTGTAAAAG
    CGAATCTAAC   TTATGTACGT   ATGTTTCCGT   AGTTGCGTCC   TATTGGTGTA   ACACATTTTC
       2170        2180         2190         2200         2210         2220
    GGGCAGCAAA   ACCCAAAGA    CCCACAATTC   GTTGACATAC   TTTCCAATCA   ATAGGCCTGT
    CCCGTCGTTT   TGGGTTTTCT   GGGTGTTAAG   CAACTGTATG   AAAGGTTAGT   TATCCGGACA
       2230        2240         2250         2260         2270         2280
    TAATAGGAAG   TTTTCTAAAA   CATTCTTTGA   TTTTTTGTAT   GATGTGTTCT   TGTGGCAAGG
    ATTATCCTTC   AAAAGATTTT   GTAAGAAACT   AAAAAACATA   CTACACAAGA   ACACCGTTCC
       2290        2300         2310         2320         2330         2340
    ACCCATAACA   TCCAATGACA   TAACCCATAA   AATTTAGAGA   GTAACCCCAT   CTCTTTGTTT
    TGGGTATTGT   AGGTTACTGT   ATTGGGTATT   TTAAATCTCT   CATTGGGGTA   GAGAAACAAA
       2350        2360         2370         2380         2390         2400
    TGTTAGGGTT   TAAATGTATA   CCCAAAGACA   AAAGAAAATT   GGTAACAGCG   GTAAAAAGGG
    ACAATCCCAA   ATTTACATAT   GGGTTTCTGT   TTTCTTTTAA   CCATTGTCGC   CATTTTTCCC
       2410        2420         2430         2440         2450         2460
    ACTCAAGATG   CTGTACAGAC   TTGGCCCCCA   ATACCACATC   ATCCATATAA   CTGAAAGCCA
    TGAGTTCTAC   GACATGTCTG   AACCGGGGGT   TATGGTGTAG   TAGGTATATT   GACTTTCGGT
       2470        2480         2490         2500         2510         2520
    AACAGTGGGG   GAAAGCCCTA   CGAACCACTG   AACAAATGGC   ACTAGTAAAC   TGAGCCAGGA
    TTGTCACCCC   CTTTCGGGAT   GCTTGGTGAC   TTGTTTACCG   TGATCATTTG   ACTCGGTCCT t"S"
```

Fig. 2B.

```
      2530       2540       2550       2560       2570       2580
  GAAACGGGCT GAGGCCCACT CCCATAGGAA TTTTCCGAAA GCCCAGGATG ATGGGATGGG
  CTTTGCCCGA CTCCGGGTGA GGGTATCCTT AAAAGGCTTT CGGGTCCTAC TACCCTACCC
      2590       2600       2610       2620       2630       2640
  AATACAGGTG CAATTTCCGT CCGAAGGTTT GGTACAGCAA CAGGAGGGAT ACATAGAGGT
  TTATGTCCAC GTTAAAGGCA GGCTTCCAAA CCATGTCGTT GTCCTCCCTA TGTATCTCCA
      2650       2660       2670       2680       2690       2700
  TCCTTGAGCA GTAGTCATGC AGGTCCGGCA TGGTCCCGTG CTGGTTGTTG AGGATCCTGG
  AGGAACTCGT CATCAGTACG TCCAGGCCGT ACCAGGGCAC GACCAACAAC TCCTAGGACC
      2710       2720       2730       2740       2750       2760
  AATTAGAGGA CAAACGGGCA ACATACCTTG ATAGTCCAGA AGAACCAACA AGAAGATGAG
  TTAATCTCCT GTTTGCCCGT TGTATGGAAC TATCAGGTCT TCTTGGTTGT TCTTCTACTC
      2770       2780       2790       2800       2810       2820
  GCATAGCAGC AGGATGAAGA GGAAGATGAT AAAACGCCGC AGACACATCC AGCGATAACC
  CGTATCGTCG TCCTACTTCT CCTTCTACTA TTTTGCGGCG TCTGTGTAGG TCGCTATTGG
      2830       2840       2850       2860       2870       2880
  AGGACAAGTT GGAGGACAAG AGGTTGGTGA GTGATTGGAG GTTGGGGACT GCGAATTTTG
  TCCTGTTCAA CCTCCTGTTC TCCAACCACT CACTAACCTC CAACCCCTGA CGCTTAAAAC
      2890       2900       2910       2920       2930       2940
  GCCAAGACAC ACGGTAGTTC CCCCTAGAAA ATTGAGAGAA GTCCACCACG AGTCTAGACT
  CGGTTCTGTG TGCCATCAAG GGGGATCTTT TAACTCTCTT CAGGTGGTGC TCAGATCTGA
      2950       2960       2970       2980       2990       3000
  CTGCGGTATT GTGAGGATTC TTGTCAACAA GAAAAACCCC GCCTGTAACA CGAGAAGGGG
  GACGCCATAA CACTCCTAAG AACAGTTGTT CTTTTTGGGG CGGACATTGT GCTCTTCCCC
      3010       3020       3030       3040       3050       3060
  TCCTAGGAAT CCTGATGTGA TGTTCTCCAT GTTCAGCGCA GGGTCCCCAA TCCTCGAGAA
  AGGATCCTTA GGACTACACT ACAAGAGGTA CAAGTCGCGT CCCAGGGGTT AGGAGCTCTT
      3070       3080       3090       3100       3110       3120
  GATTGACGAT AAGGGAGAGG CAGTAGTCAG AACAGGGTTT ACTGTTCCTG AACTGGAGCC
  CTAACTGCTA TTCCCTCTCC GTCATCAGTC TTGTCCCAAA TGACAAGGAC TTGACCTCGG
                              HincII(2963)   HhaI(3036)
                                       pS        AvaI(3053)
```

Fig.2C.

```
       3130       3140       3150       3160       3170       3180
  ACCAGCAGGG AAATACAGGC CTCTCACTCT GGGATCTTGC AGAGTTTGGT GGAAGGTTGT
  TGGTCGTCCC TTTATGTCCG GAGAGTGAGA CCCTAGAACG TCTCAAACCA CCTTCCAACA

GG  L 3'                                              f2
  CC  S 5'                                          ←———————
     ↘
      EcoRI (1/3182)
```

```
                                                            30
3' TAC  CTC  TTG  TAG  TGT  AGT  CCT  AAG  GAT  CCT
5' ATG  GAG  AAC  ATC  ACA  TCA  GGA  TTC  CTA  GGA
   MET  GLU  ASN  ILE  THR  SER  GLY  PHE  LEU  GLY
                                                            60
   GCG  GAA  GAG  CAC  AAT  GTC  CGC  CCC  AAA  AAG
   CCC  CTT  CTC  GTG  TTA  CAG  GCG  GGG  TTT  TTC
   PRO  LEU  LEU  VAL  LEU  GLN  ALA  GLY  PHE  PHE
                                                            90
   AAC  AAC  TGT  TCT  TAG  GAG  TGT  TAT  GGC  GTC
   TTG  TTG  ACA  AGA  ATC  CTC  ACA  ATA  CCG  CAG
   LEU  LEU  THR  ARG  ILE  LEU  THR  ILE  PRO  GLN
                                                           120
   TCA  GAT  CTG  AGC  ACC  ACC  TGA  AGA  GAG  TTA
   AGT  CTA  GAC  TCG  TGG  TGG  ACT  TCT  CTC  AAT
   SER  LEU  ASP  SER  TRP  TRP  THR  SER  LEU  ASN
                                                           150
   AAA  GAT  CCC  CCT  TGA  TGG  CAC  ACA  GAA  CCG
   TTT  CTA  GGG  GGA  ACT  ACC  GTG  TGT  CTT  GGC
   PHE  LEU  GLY  GLY  THR  THR  VAL  CYS  LEU  GLY
                                                           180
   GTT  TTA  AGC  GTC  AGG  GGT  TGG  AGG  TTA  GTG
   CAA  AAT  TCG  CAG  TCC  CCA  ACC  TCC  AAT  CAC
   GLN  ASN  SER  GLN  SER  PRO  THR  SER  ASN  HIS
                                                           210
   AGT  GGT  TGG  AGA  ACA  GGA  GGT  TGA  ACA  GGA
   TCA  CCA  ACC  TCT  TGT  CCT  CCA  ACT  TGT  CCT
   SER  PRO  THR  SER  CYS  PRO  PRO  THR  CYS  PRO
                                                           240
   CCA  ATA  GCG  ACC  TAC  ACA  GAC  GCC  GCA  AAA
   GGT  TAT  CGC  TGG  ATG  TGT  CTG  CCG  CGT  TTT
   GLY  TYR  ARG  TRP  MET  CYS  LEU  ARG  ARG  PHE
```

Fig.3B.

```
                                                        270
TAG  TAG  AAG  GAG  AAG  TAG  GAC  GAC  GAT  ACG
ATC  ATC  TTC  CTC  TTC  ATC  CTG  CTG  CTA  TGC
ILE  ILE  PHE  LEU  PHE  ILE  LEU  LEU  LEU  CYS
                                                        300
GAG  TAG  AAG  AAC  AAC  CAA  GAA  GAC  CTG  ATA
CTC  ATC  TTC  TTG  TTG  GTT  CTT  CTG  GAC  TAT
LEU  ILE  PHE  LEU  LEU  VAL  LEU  LEU  ASP  TYR
                                                        330
GTT  CCA  TAC  AAC  GGG  CAA  ACA  GGA  GAT  TAA
CAA  GGT  ATG  TTG  CCC  GTT  TGT  CCT  CTA  ATT
GLN  GLY  MET  LEU  PRO  VAL  CYS  PRO  LEU  ILE
     Site BamHI                                         360
GGT  CCT  AGG  AGT  TGT  TGG  TCG  TGC  CCT  GGT
CCA  GGA  TCC  TCA  ACA  ACC  AGC  ACG  GGA  CCA
PRO  GLY  SER  SER  THR  THR  SER  THR  GLY  PRO
                                                        390
ACG  GCC  TGG  ACG  TAC  TGA  TGA  CGA  GTT  CCT
TGC  CGG  ACC  TGC  ATG  ACT  ACT  GCT  CAA  GGA
CYS  ARG  THR  CYS  MET  THR  THR  ALA  GLN  GLY
                                                        420
TGG  AGA  TAC  ATA  GGG  AGG  ACA  ACG  ACA  TGG
ACC  TCT  ATG  TAT  CCC  TCC  TGT  TGC  TGT  ACC
THR  SER  MET  TYR  PRO  SER  CYS  CYS  CYS  THR
                                                        450
TTT  GGA  AGC  CTG  CCT  TTA  ACG  TGG  ACA  TAA
AAA  CCT  TCG  GAC  GGA  AAT  TGC  ACC  TGT  ATT
LYS  PRO  SER  ASP  GLY  ASN  CYS  THR  CYS  ILE
                                                        480
GGG  TAG  GGT  AGT  AGG  ACC  CGA  AAG  CCT  TTT
CCC  ATC  CCA  TCA  TCC  TGG  GCT  TTC  GGA  AAA
PRO  ILE  PRO  SER  SER  TRP  ALA  PHE  GLY  LYS
```

Fig.3C.

```
                                              510
AAG  GAT  ACC  CTC  ACC  CGG  AGT  CGG  GCA  AAG
TTC  CTA  TGG  GAG  TGG  GCC  TCA  GCC  CGT  TTC
                        Site HaeIII
PHE  LEU  TRP  GLU  TRP  ALA  SER  ALA  ARG  PHE
                                              540
AGG  ACC  GAG  TCA  AAT  GAT  CAC  GGT  AAA  CAA
TCC  TGG  CTC  AGT  TTA  CTA  GTG  CCA  TTT  GTT
SER  TRP  LEU  SER  LEU  LEU  VAL  PRO  PHE  VAL
                                              570
GTC  ACC  AAG  CAT  CCC  GAA  AGG  GGG  TGA  CAA
CAG  TGG  TTC  GTA  GGG  CTT  TCC  CCC  ACT  GTT
GLN  TRP  PHE  VAL  GLY  LEU  SER  PRO  THR  VAL
                                              600
ACC  GAA  AGT  CAA  TAT  ACC  TAC  TAC  ACC  ATA
TGG  CTT  TCA  GTT  ATA  TGG  ATG  ATG  TGG  TAT
TRP  LEU  SER  VAL  ILE  TRP  MET  MET  TRP  TYR
                                              630
ACC  CCC  GGT  TCA  GAC  ATG  TCG  TAG  AAC  TCA
TGG  GGG  CCA  AGT  CTG  TAC  AGC  ATC  TTG  AGT
TRP  GLY  PRO  SER  LEU  TYR  SER  ILE  LEU  SER
                                              690
GGG  AAA  AAT  GGC  GAC  AAT  GGT  TAA  AAG  AAA
CCC  TTT  TTA  CCG  CTG  TTA  CCA  ATT  TTC  TTT
PRO  PHE  LEU  PRO  LEU  LEU  PRO  ILE  PHE  PHE ACA  GAA  ACC  CAT  ATG  TAA  ATT  5'
TGT  CTT  TGG  GTA  TAC  ATT  TAA  3'
CYS  LEU  TRP  VAL  TYR  ILE  STOP
```

Fig.4A.

```
                                      2191      2200       2210       2220
                                   5' TTGACATAC TTTCCAATCA ATAGGCCTGT
                                   3' AACTGTATG AAAGGTTAGT TATCCGGACA
    2230       2240       2250       2260       2270       2280
 TAATAGGAAG TTTTCTAAAA CATTCTTTGA TTTTTTGTAT GATGTGTTCT TGTGGCAAGG
 ATTATCCTTC AAAAGATTTT GTAAGAAACT AAAAAACATA CTACACAAGA ACACCGTTCC
    2290       2300       2310       2320       2330       2340
 ACCCATAACA TCCAATGACA TAACCCATAA AATTTAGAGA GTAACCCCAT CTCTTTGTTT
 TGGGTATTGT AGGTTACTGT ATTGGGTATT TTAAATCTCT CATTGGGGTA GAGAAACAAA
    2350       2360       2370       2380       2390       2400
 TGTTAGGGTT TAAATGTATA CCCAAAGACA AAAGAAAATT GGTAACAGCG GTAAAAAGGG
 ACAATCCCAA ATTTACATAT GGGTTTCTGT TTTCTTTTAA CCATTGTCGC CATTTTTCCC
    2410       2420       2430       2440       2450       2460
 ACTCAAGATG CTGTACAGAC TTGGCCCCCA ATACCACATC ATCCATATAA CTGAAAGCCA
 TGAGTTCTAC GACATGTCTG AACCGGGGGT TATGGTGTAG TAGGTATATT GACTTTCGGT
    2470       2480       2490       2500       2510       2520
 AACAGTGGGG GAAAGCCCTA CGAACCACTG AACAAATGGC ACTAGTAAAC TGAGCCAGGA
 TTGTCACCCC CTTTCGGGAT GCTTGGTGAC TTGTTTACCG TGATCATTTG ACTCGGTCCT
    2530       2540       2550       2560       2570       2580
 GAAACGGGCT GAGGCCCACT CCCATAGGAA TTTTCCGAAA GCCCAGGATG ATGGGATGGG
 CTTTGCCCGA CTCCGGGTGA GGGTATCCTT AAAAGGCTTT CGGGTCCTAC TACCCTACCC
    2590       2600       2610       2620       2630       2640
 AATACAGGTG CAATTTCCGT CCGAAGGTTT GGTACAGCAA CAGGAGGGAT ACATAGAGGT
 TTATGTCCAC GTTAAAGGCA GGCTTCCAAA CCATGTCGTT GTCCTCCCTA TGTATCTCCA
    2650       2660       2670       2680       2690       2700
 TCCTTGAGCA GTAGTCATGC AGGTCCGGCA TGGTCCCGTG CTGGTTGTTG AGGATCCTGG
 AGGAACTCGT CATCAGTACG TCCAGGCCGT ACCAGGGCAC GACCAACAAC TCCTAGGACC
    2710       2720       2730       2740       2750       2760
 AATTAGAGGA CAAACGGGCA ACATACCTTG ATAGTCCAGA AGAACCAACA AGAAGATGAG
 TTAATCTCCT GTTTGCCCGT TGTATGGAAC TATCAGGTCT TCTTGGTTGT TCTTCTACTC
    2770       2780       2790       2800       2810       2820
 GCATAGCAGC AGGATGAAGA GGAAGATGAT AAAACGCCGC AGACACATCC AGCGATAACC
 CGTATCGTCG TCCTACTTCT CCTTCTACTA TTTTGCGGCG TCTGTGTAGG TCGCTATTGG
```

Fig.4B.

```
      2830        2840        2850        2860        2870        2880
 AGGACAAGTT  GGAGGACAAG  AGGTTGGTGA  GTGATTGGAG  GTTGGGGACT  GCGAATTTTG
 TCCTGTTCAA  CCTCCTGTTC  TCCAACCACT  CACTAACCTC  CAACCCCTGA  CGCTTAAAAC
      2890        2900        2910        2920        2930        2940
 GCCAAGACAC  ACGGTAGTTC  CCCCTAGAAA  ATTGAGAGAA  GTCCACCACG  AGTCTAGACT
 CGGTTCTGTG  TGCCATCAAG  GGGGATCTTT  TAACTCTCTT  CAGGTGGTGC  TCAGATCTGA
      2950        2960
 CTGCGGTATT  GTGAGGATTC  TTG  L  3'
 GACGCCATAA  CACTCCTAAG  AAC  S  5'
```

$\xleftarrow{\quad f_2 \quad}$

Fig.5.

```
                     24                            30
                    ARG  ILE  LEU  THR  ILE  PRO  GLN  SER  LEU  ASP  SER  TRP
                     40                                                      50
TRP  THR  SER  LEU  ASN  PHE  LEU  GLY  GLY  THR  THR  VAL  CYS  LEU  GLY
                                                  60
GLN  ASN  SER  GLN  SER  PRO  THR  SER  ASN  HIS  SER  PRO  THR  SER  CYS
                     70                                                      80
PRO  PRO  THR  CYS  PRO  GLY  TYR  ARG  TRP  MET  CYS  LEU  ARG  ARG  PHE
                                                  90
ILE  ILE  PHE  LEU  PHE  ILE  LEU  LEU  LEU  CYS  LEU  ILE  PHE  LEU  LEU
                     100                                                     110
VAL  LEU  LEU  ASP  TYR  GLN  GLY  MET  LEU  PRO  VAL  CYS  PRO  LEU  ILE
                                                  120
PRO  GLY  SER  SER  THR  THR  SER  THR  GLY  PRO  CYS  ARG  THR  CYS  MET
                     130                                                     140
THR  THR  ALA  GLN  GLY  THR  SER  MET  TYR  PRO  SER  CYS  CYS  CYS  THR
                                                  150
LYS  PRO  SER  ASP  GLY  ASN  CYS  THR  CYS  ILE  PRO  ILE  PRO  SER  SER
                     160                                                     170
TRP  ALA  PHE  GLY  LYS  PHE  LEU  TRP  GLU  TRP  ALA  SER  ALA  ARG  PHE
                                                  180
SER  TRP  LEU  SER  LEU  LEU  VAL  PRO  PHE  VAL  GLN  TRP  PHE  VAL  GLY
                     190                                                     200
LEU  SER  PRO  THR  VAL  TRP  LEU  SER  VAL  ILE  TRP  MET  MET  TRP  TYR
                                                  210
TRP  GLY  PRO  SER  LEU  TYR  SER  ILE  LEU  SER  PRO  PHE  LEU  PRO  LEU
                     220                                      226
LEU  PRO  ILE  PHE  PHE  CYS  LEU  TRP  VAL  TYR  ILE
```

Fig.6.

```
                                                    f2 →
                                    AGG AGT TGT TGG TCG TGC CCT GGT  360
                                    TCC TCA ACA ACC AGC ACG GGA CCA
                                    SER SER THR THR SER THR GLY PRO  420
ACG GCC TAC TGA CGA GTT CCT TGG AGA TAC ATA GGG ACA ACG ACA TGG
TGC CGG ATG ACT GCT CAA GGA ACC TCT ATG TAT CCC TGT TGC ACA ACC
CYS ARG MET THR ALA GLN GLY THR SER MET TYR PRO CYS CYS CYS THR
                                390
TTT GGA AGC CTG CCT TTA ACG TGG ACA TAG AGT GGT ACC AGG ACC CTT  480
AAA CCT TCG GAC CTG AAT TGC ACC TGT ATC TCA CCA TCC CGA AAG GGA AAA
LYS PRO SER ASP GLY ASN CYS THR CYS ILE PRO SER TRP SER GLY ALA PHE GLY LYS

AAG GAT ACC CTC ACC
TTC CTA TGG GAG TGG
PHE LEU TRP GLU TRP
```

NUCLEOTIDIC SEQUENCE CODING THE SURFACE ANTIGEN OF THE HEPATITIS B VIRUS, VECTOR CONTAINING SAID NUCLEOTIDIC SEQUENCE, PROCESS ALLOWING THE OBTENTION THEREOF AND ANTIGEN OBTAINED THEREBY

The invention relates to a nucleic acid comprising a nucleotide sequence capable of coding an immunogenic peptide sequence corresponding to the surface antigen of the virus of viral hepatitis B, and to the polypeptides and peptides obtained.

It relates also to a process enabling such a nucleic acid to be obtained.

Hepatitis B is a frequent viral disease particularly in Tropical Africa, in South East Asia and in the Far East.

The etiological agent is a virus (HBV) or Dane particle, comprising an envelope (Australia antigen or HBs antigen), a capsid (HBc antigen), and endogenic polymerase and a partly single strand circular DNA molecule; the longest strand of this DNA molecule includes close to 3,200 nucleotides (SUMMERS J., O'CONNELL / A. et MILLMAN I. (1975) Proc. Nat. Acad. Sci. USA 72, 4 597–4 601).

The endogenic DNA polymerase can be used to repair the shorter strand in vitro (T. A. LANDERS, H. B. GREENBERT and J. S. ROBINSON, J. VIROL., 23, 1977, p. 368–376).

Electrophoretic analysis of the proteins of the envelope has shown the presence of 2 to 7 polypeptides of which the principal are called: polypeptide I and polypeptide II (PETERSON D. L., ROBERTS I. M. and VYAS G. N. (1977) Proc. Nat. Acad. Sci., USA, 74, 1,530–1,534, and PETERSON D. L., CHIEN D. Y., VYAS G. N., NITECHKI D. and BOND H. (1978) In viral Hepatitis, ed. G. VYAS, S. COHEN and R. SCHMID, The Franklin Institute Press, Philadelphia, 569–573).

The Polypeptide I has a weight of 22,000 to 26,000 daltons. Polypeptide II is glycosylated and has a molecular weight of 28,000 to 30,000 daltons. The amino acid composition of these two polypeptides is very similar, the sequences which form, respectively, their 15 first amino-acids (from the N-terminal end) and their last 3 amino-acids are identical, so that the hypothesis has formulated that polypeptide II could differ from polypeptide I only by a glycosylation.

Study of the virus is extremely difficult to the extent that no cell culture system is available enabling the propagation of the virus. This difficulty has already in part been overcome, more particularly as regards the ayw serotype. The whole DNA (genome) of the virus has been identified and cloned, notably in *E. coli*, after its previous insertion in the single EcoRI site of a λgt.WES. λB vector, according to the technique by FRITSCH A., POURCEL C., CHARNAY P. and TIOLLAIS P. (1978) C. R. Acad. de Paris, 287, 1,453–1,456).

Until now, the sequence of the I and II polypeptides themselves, and the location in the viral DNA of the sequence coding these peptides have not been done.

It is an object of the invention to provide a much smaller DNA sequence than the viral DNA itself, containing the sequence adapted to code the peptide sequence endowed with immunogenic properties enabling, when it is introduced into the organism of a living host, to induce the formation by the latter of antibodies capable of protecting this same host subsequently with respect to the virus of viral hepatitus B, notably when the latter is in virulent state.

The invention stems not only from the complete nucleotide analysis of the genome of the Dane particle which the inventors have achieved, but to the idea that they have had for identifying the coding gene (called below "S gene") of the abovesaid polypeptides, to search in the complete nucleotide structure thus preestablished of the genome of the Dane particle, for those of the sequences of the nucleotides capable of coding the known proximal and terminal peptide sequences of these polypeptides.

It will be recalled the PETERSON and co-workers have reported, notably in the articles of which the references are recalled above, that the proximal sequence (first N-terminal amino-acid) of the 15 first amino-acids is in principle as follows: met glu asn ile thr ser gly phe leu gly pro leu leu val ser and that the terminal sequence of these same polypeptides (last C-terminal amino-acid) was the following:

val tyr ile

FIG. 2 is a diagramatic chart of a vector;

FIGS. 1a–1h illustrate diagramatically the steps in the manufacture of a vector plasmid type incorporating a fragment of HBV DNA;

FIG. 3a, 3b and 3c show the nucleotide structure of the gene S and the polypeptide chain resulting from the translation of the gene;

FIG. 4a and 4b show the two mutually complementary strands of DNA sequence;

FIG. 5 shows the peptidic sequence coded by nucleotide sequence, and

FIG. 6 shows a nucleotide containing a peptide sequence according to the invention.

FIG. 1 is a diagrammatic chart of the genome of the Dane particle. The latter includes two strands $b_1$ and $b_2$; the shortest of them ($b_2$) being normally devoid of the portion represented by an interrupted line in the drawing.

It is known that this DNA only includes a single EcoRI site.

The arrow $f_1$ gives the direction of numbering of the nucleotides from which the longest strand $b_1$ is composed, and the arrow $f_2$ gives the direction of the transcription of the DNA of the virus, notably by the cellular mechanism of the cells invaded by the virus of hepatitis B, as regards the expression of the gene S.

The EcoRI site can hence be numbered 0 or, as has now been determined more exactly for that of the hepatitis B virus belonging to the serotype ayw, 3,182.

The inner circle e in continuous line gives the scale in % of the length of the DNA and permits the positions of certain of its parts to be specified.

The numbers 3', 5' and 5', 3' at the lower part of the chart are aimed at the terminal ends bearing the same numbers in conventional representation of the ends of the nucleic acid chains.

Figure 1:
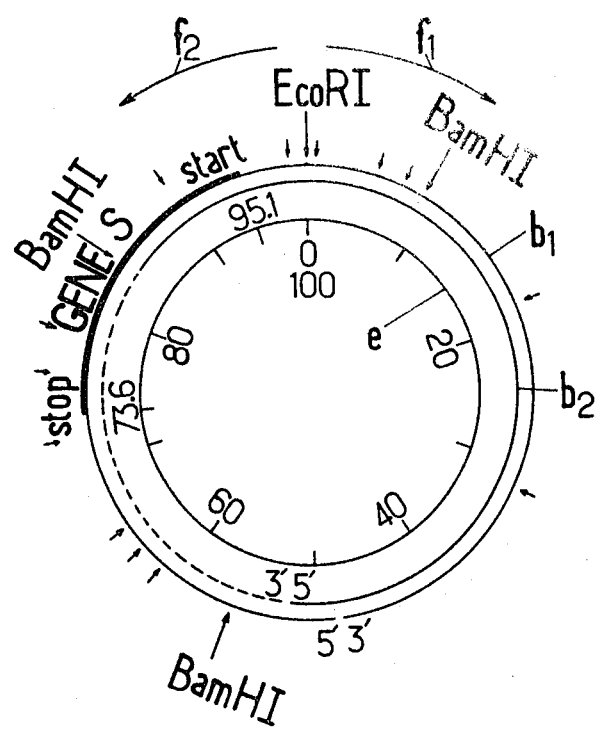
FIG. 1 is a diagramatic chart of the genome of the Dane particle.

According to the invention it has been shown that the "gene S" constituted essentially the fragment of the longest strand $b_1$ situated between the positions 73.6 and 95.1 of the diagrammatic map of FIG. 1. The abbreviations "Start" and "Stop" represent the initiation and stopping points of the transcription of the "gene S".

Figure 2A:
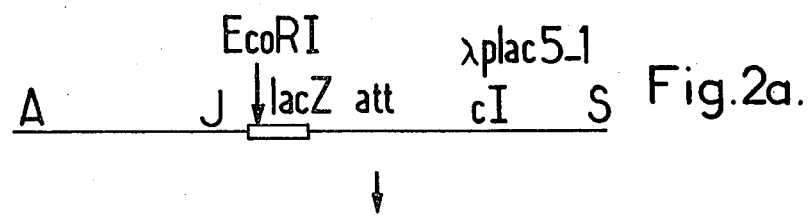
FIG. 2a is a diagramatic chart of a vector.
Figure 2B:
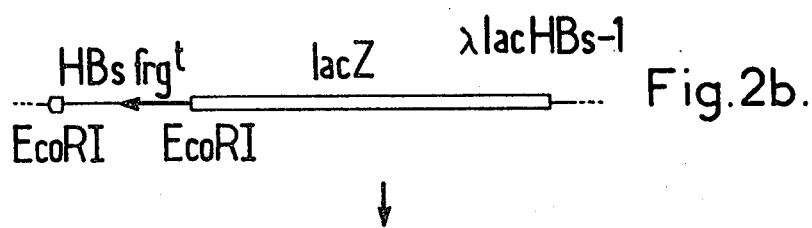
FIG. 2b is a diagramatic chart of FIG. 2a showing the modification introduced into its gene Z.
Figure 2C:
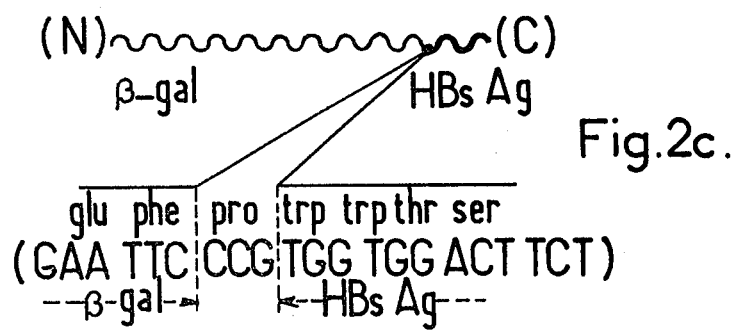
FIG. 2c shows a diagramatic structure of the hybrid polypeptide obtained as a result of the expression of the modified vector of FIG. 2b.

FIGS. 2A, 2B, 2C are representative of the terminal portion of the abovesaid genome, comprised notably between the positions 60.4 and 100 (in % length of DNA). Each of the letters shown in FIG. 2 correspond conventionally to one of the 4 basic nucleotides of DNA:

A: Adenine
G: Guanine
T: Thymine
C: Cytosine

The lower lines, in each pair of lines from which FIGS. 2A, 2B, 2C are constituted, correspond to the nucleic acid corresponding to the nucleotide chain $b_2$.

The analytical technique used to establish the more detailed map represented by FIGS. 2A, 2B, 2C, will be briefly recalled below.

The characterisation of the nucletide of the "gene S" such as proposed within the scope of the present invention, and of which the proximal ends p "S" and terminal ends t "S" are indicated in FIGS. 2A, 2B, 2C, results from the observation that:

the first 14 triplets (in the direction of reading $f_2$) from the nucleotide numbered 3 030 with respect to the EcoRI terminal end, are respectively capable of coding the 14 first amino-acids of the proximal sequence of the 15 first amino-acids of the abovesaid polypeptides, the 4 last triplets GTA TAC ATT TAA read in the complementary chain $b_2$ to the transcribed chain $b_1$ correspond respectively to the 3 terminal amino-acids of the abovesaid polypeptides and to a stop codon;

this sequence of nucleotides (678 nucleotides) does not comprise any stop codon, at least when the reading frame is adopted implying that the first triplet "read" on the DNA by the cellular mechanism is AUG, (corresponding to a strand complementary to ATG);

the complete translation of the genetic information commencing with the initial codon ATG leads to a theoretical polypeptide of 226 amino-acids, having a molecular weight of 25, 422 daltons.

The nucleotide structure of the "gene S" as well as the polypeptide chain resulting from the translation of the "gene S" are shown in FIGS. 3A, 3B, 3C.

These values are quite in accordance with the analytical data which result from the electrophoretic mobility of the polypeptide I on polyacrylamide gels which have already been described by the preceding authors (references 9-12 according to the bibliography figuring at the end of the description of the present patent application).

The difference observed at the level of the 15th amino-acid of the proximal peptide sequence of the polypeptide I: leucine according to the charts of FIGS. 2A, 2B, 2C, and 3A, 3B, 3C mentioned above, and not serine according to the observation of the abovesaid authors, may perhaps be attributed to the fact that these authors have worked with a genetic variant different from that which is the subject of the present study. It will be noted that the difference can besides be attributed to the substitution of a single nucleotide in the "TTA" triplet concerned in the particular "gene S" shown in the maps of FIGS. 2A, 2B, 2C and 3A, 3B, 3C, instead of "TCA", one of the triplets capable of being translated into serine.

The invention hence relates more particularly to the fragments of the nucleic acid which can be excised from the DNA of the Dane particle, these fragments being more particularly characterised in that they contain the portion of the "gene S" capable of coding the portion of the protein of the envelope of the virus which is responsible for the immunological properties of the hepatitis B virus.

Accordingly, the invention relates therefore to a nucleic acid comprising at the most of the order of 1,000–1,100 nucleotides, more particularly characterised in that it is adapted to code an immunogenic peptide sequence, itself adapted to induce in vivo the production of active antibodies with respect to the hepatitis B virus, this peptide sequence containing essentially the structure shown in FIGS. 3A, 3B, 3C, or any peptide sequence having equivalent immunogenic properties.

The invention also relates to a vector for the expression of said nucleotide sequence into a micro-organism or into eucaryotic cells on condition that the genetic fusion has been carried out by preserving the reading phase of the "gene S".

The nucleotide sequences used according to the invention have with respect to one another a variability leading, on their expression, to the formation of determinants varying according to the sub-type of the hepatitis B virus (sub-types d, w, y, r of group a).

For one of the peptide sequences shown in FIGS. 3A, 3B, 3C, it will be observed that the first amino-acid of the abovesaid sequence: methionine, is N-terminal and that the amino-acid of the opposite end: isoleucine, is C-terminal.

The invention also relates, more particularly, to the nucleotide sequence represented in FIGS. 4A, 4B, coding the peptide sequence such as results from FIG. 5 or any similar peptide sequence endowed with equivalent immunogen properties.

It is self-evident that by "equivalent peptide sequence", mentioned above, must be understood any peptide sequence in which certain parts may not be strictly identical with corresponding parts of the peptide sequence shown in FIGS. 3A, 3B, 3C and 5, these variations being attributable to local mutations not affecting the general immunogen character of the protein or with structural modifications owing to the different serotypes in which proteins of the type concerned can occur (notably serotypes adw, adr and ayr).

The invention relates more particularly to the nucleotide sequence containing the peptide sequence as shown in FIG. 6 or any similar peptide sequence endowed with equivalent immunogen properties.

The invention relates more particularly again to the following peptide sequences:

Alanine-Glutamine-Glycine-Threonine-Serine
Threonine-Alanine-Glutamine-Glycine-Threonine-Serine
Threonine-Threonine-Alanine-Glutamine-Glycine-Threonine-Serine In the first above-indicated peptide the alanine end is N-terminal and the serine end is C-terminal.

In the second or third abovementioned peptides, the threonine end is N-terminal and the serine end is C-terminal.

By way of example, it is possible notably to prepare the pentapeptide starting from the C-terminal serine to which threonine is fastened by the Castro method described in Tetrahedron Letters, 1975, No. 14, page 1,219–1,222. Then the amino-acids glycine, glutamine, alanine are added by the so-called repeated mixed anhydride method (rema method) described by Beierman in Chemistry and Biology of Peptides, Ed. J. Meienhofer, Ann. Arbour Science Publ., Ann. Arb. Mich. 341 (1972).

The invention also relates to the products resulting from the fixing of the pentapeptide on to a larger carrier molecule, notably of the polypeptide or protein type, the composition containing this pentapeptide in fixing products, notably in association with a pharmaceutically acceptable vehicle, and more particularly vaccines against hepatitis B. These pharmaceutical vehicles are suited, conventionally, to the selected method of administration, notably orally, parenterally, rectally or by nebulisation on to the mucous membranes, notably the nasal membranes.

The hexapeptide and the polypeptide with 7 aminoacids can be synthesized by conventional peptide synthesis techniques.

These peptides are, according to the present invention, believed to be the antigen site of the polypeptides of larger size considered above and responsible for the vaccinating power of the viral envelope (Journal of Biol. Stand. 1976, 4, 295–304, RAO et VYAS "Biochemical Characterization of Hepatitis B Surface Antigen in Relation to Serologic Activity").

Again the invention relates also to the DNA fragments capable of coding the production of such pentapeptide, hexapeptide and polypeptide with 7 amino acids. It relates to:

for the pentapeptide, notably the polynucleotide of the formula:

5' CCT CAA GGA ACC TCT 3'

3' GGA GTT CCT TGG AGA 5' for the hexapeptide, notably of the polynucleotide of the formula:

5' ACT GCT CAA GGA ACC TCT 3'

3' TGA CGA GTT CCT TGG AGA 5' for the polypeptide with 7 amino acids the polynucleotide of the formula:

5' ACT ACT GCT CAA GGA ACC TCT 3'

3' TGA TGA CGA GTT CCT TGG AGA 5' or in each of the three cases, of the complementary polynucleotide relating to the three preceding respective polynucleotides or again any polynucleotide in which each of the triplets can be replaced by any similar triplet capable of coding the production of the same amino-acid.

The nucleic acid according to the invention can also be characterised in that it comprises at least one of the two mutually complementary strands of a DNA sequence such as shown in FIGS. 4A, 4B (in which are shown also the numbers corresponding to the positions of the first nucleotides of each of the successive fragments of 10 nucleotides shown with respect to the EcoRI position not shown in the Figure; it is self-evident that these numbers do not come into consideration at the level of characterisation of the nucleotide sequence of the type concerned). This DNA fragment is bounded by two sites.

It will be appreciated that this nucleotide sequence corresponds to the genetic information whose translation leads to the peptide sequence shown in FIG. 5.

The invention relates naturally to equivalent nucleotide sequences with a single strand or double strand, of which notably the strand having the structure which arises from the succession of lower lines of FIGS. 4A, 4B, the corresponding double strand DNA, or the corresponding messenger RNA's, notably that shown by the complementary chains of nucleotides constituted by the lower lines of the pairs of lines of FIGS. 4A, 4B (direction of the arrow $f_2$).

In the same way there come within the field of the invention the nucleotide chains which are differentiated from the preceding ones by certain triplets or small sequences of triplets, to the extent that these nucleotide sequences remain adapted to code a polypeptide preserving the characteristic immunogen activities of the virus of viral hepatitis B. In general, it relates to nucleotide chains which, possibly, after denaturation of the double strand DNA to produce the corresponding single strand nucleic acids, remain capable of hybridizing over at least about 90% of their length with one of the DNA strands of FIGS. 4A, 4B.

Preferred nucleic acids according to the invention are also those which can be excised from DNA of viral hepatitis and which, when they are double strand, are characterised by the existence at one of their ends of an HincII, HhaI, AvaI or EcoRI extremity and at their other end by an AvaIII, HincII or HhaI extremity.

The positions of these various extremities with respect to the EcoRI site are shown diagrammatically in FIGS. 2A, 2B, 2C.

The nucleic acid according to the invention is intended for incorporation in a vector enabling its expression into a bacteria and into eucaryotic cells, notably for the production of a protein or of a peptide capable of inducing in the organism of a living host the production of active antibodies against the virus of viral hepatitis B. The protein or peptide resulting from the translation of the nucleotide sequence according to the invention can be used as a vaccinating agent or as an agent serving for diagnosis.

The nucleic acid according to the invention can also be used as a probe to track down the presence or not in blood samples or test serum, of the Dane particle, of the HBs antigen or of fragments of the latter, etc. (by the conventional DNA-DNA hybridization technique).

Other characteristics of the invention will result also from the brief description which follows of the techniques of analysis of identification and of production of DNA fragments according to the invention. Reference will naturally be made to the drawings whose Figures have already been taken into consideration in the foregoing. The FIgures or numbers between parentheses correspond to the references of the bibliography appended to the present description.

The invention relates also to particular vectors enabling the expression of the above-described nucleotide sequences, notably in the form of a hybrid protein in which a protein fragment having the immunological character of HBsAg added to a carrier molecule conferring on the whole immunogen or immunoreactive properties, capable of inducing the production of protective antibodies with respect to viral infection in the organism of the host into which this protein has previously been introduced.

In particular, the invention relates to a vector—phage or plasmid—containing at least a part of the lactose operon, more particularly the promoter and the Z gene of this operon, this vector being characterised in that it is modified for the insertion, in phase, in a suitable site of the Z gene, such as the EcoRI site of any one of the DNA fragments of the principal patent, notably those containing the largest part of the "S gene". It relates also to those of these modified vectors, in which a part at least of the coding DNA fragment for the largest part of the β-galactosidase would be replaced by a DNA fragment adapted to code for any other non-immunogenic carrier molecule, or of which the possible immunological properties, if the latter exist, do not interfere with those of the peptide part having the immunological properties of HBsAg, for example essentially that which extends in the direction of reading from its HhaI site.

The invention relates also more particularly to a hybrid protein characterised in that it contains polypeptide sequence having the specific immunological properties of HBsAg, contiguous with a polypeptide sequence constituted for the most part of β-galactosidase, which plays the role of carrier-protein.

The invention does not extend only to this particular hybrid molecule, whose essential role is to constitute a model of a protein constructed according to the techniques of genetic engineering and endowed with immunogen and immunoreactive properties characteristic of the HBsAg antigen, but also to any other hybrid protein in which all or part of the β-galactosidase may be replaced by any other nonimmunogen carrier molecule, or of which the possible immunological properties, if the latter exist, do not interfere with those of the peptide part having the immunological properties of HBsAg.

Other characteristics of the invention will appear also in the course of the description of preferred examples, in combination with the drawings in which:

the FIGS. 1a and 1h illustrate diagrammatically the steps in the manufacture of a vector of the plasmid type incorporating a fragment of HBV DNA, FIGS. 2a to 2c illustrate diagrammatically the initial structures of the final vector used (FIG. 2a) of the modified vector obtained (FIG. 2b) and that of the hybrid protein resulting from the expression of this modified vector into E. coli. (FIG. 2c).

A—NUCLEOTIDE SEQUENCES

Products and methods used

The enzymes and chemical substances used

The restriction enzymes used: BamHI, HhaI, HincII, HaeIII, XbaI, MboI, HinfI, HpaII, XhoI, are those manufactured by BIOLABS. DNA-polymerase I of BOEHRINGER was used. The bacterial alkaline phosphatase and the polynucleotide-kinase were supplied by P. L. BIOCHEMICALS. The chemical agents were the following:

Dimethyl sulfate (ALDRICH),
Hydrazine (EASTMAN KODAK),
Acrylamide and bis-acrylamide (twice crystallized -SERVA),
Dideoxy nucleotide triphosphates and deoxynucleotide triphosphates (P. L. BIOCHEMICALS),
Piperidine (MERCK) redistilled in vacuo Preparation of DNA HBV The whole HBV genome (sub-type ayw) was cloned in E. coli by bringing into play the single EcoRI restriction site of the λgt. WES. λB vector (14). The cloned DNA is called below "Eco HBV DNA".

The recombinant bacteriophage was grown in a Petri dish on Agar and the desired DNA was extracted in manner known in itself. After digestion of the DNA by the EcoRI restriction enzyme, the Eco HBV DNA sequence was purified by ultracentrifugation, in a sucrose gradient, according to the technique described in the bibliographical references (16, 17).

Preparation of 5' $^{32}P$ labelled DNA fragments 10 to 20 picomoles of Eco HBV DNA were completely hydrolysed by the various restriction enzymes, under the conditions recommended by the manufacturer. The DNA fragments were dephosphorylated by alkaline phosphatase, the latter having then been inactivated by alkaline treatment. The DNA was then precipitated with ethanol, by the technique described in the article (18). After redissolving in a buffer based on spermidine, the DNA's were labelled at their 5' ends with an ATP {$\lambda^{32}P$ (3,000 Ci/mM manufactured by NEW ENGLAND NUCLEAR)} and with polynucleotide-kinase (according to the technique indicated in the article) (19).

The DNA restriction fragments were separated by electrophoresis on polyacrylamide gel, then eluted. The labelled ends were the subject of segregations by electrophoresis on polyacrylamide gel in manner known in itself, after restriction with another enzyme or by denaturation of the DNA fragments of the type concerned.

Determination of the structure of the nucleotide sequences of DNA

The primary structure of the double strand or single strand DNA fragments was determined essentially according to the technique described by MAXAM and GILBERT (19). Recourse was also had to the method of terminal chain inhibiters described by SANGER and al. (20) and adapted by MAAT and SMITH (21), as regards the double strand fragments labelled at one of their 5' ends.

The chemical and enzymatic reaction products were analysed by electrophoresis in gels of acrylamide in sequence at 8, 16 or 25%, of 1 mm thickness.

Analytical techniques and results

In order to determine whether the HBV genome is capable of coding the polypeptides I and II, all the HaeIII fragments (HaeIII restriction sites of the HBV genome shown in FIG. 1 by small arrows) were labelled at their 5' ends. Substantial portions of their primary structures were determined by the method of MAXAM and GILBERT. The nucleotide sequences capable of coding the proximal and terminal amino-acid sequences of the polypeptides I and II were localized in the HaeIII E and HaeIIIFF fragments, previously localized on the restriction map of the HBV genome-according to the technique described in the reference (17). It is these nucleotide sequences which have been considered as consisting of the ends of the "gene S" occupying themselves the positions 73.6 and 95.1 with respect to the EcoRI restriction site (FIG. 1) for the reasons already indicated.

The nucleotide sequence between these two positions has been analysed by resorting to known chemical techniques, notably by the chemical degradation method with hydrazine dimethyl sulfate and the method of chain termination. Recourse was had, among the various chemical reactions proposed by MAXAM and GILBERT to a partial depurination by formic acid and with cleavage by piperidine, methods which give equal intensity bands on autoradiograms for the fragments terminated by guanine and an adenine. Reactions with hydrazine followed by cleavage with piperidine were also used to obtain bands of equal intensity, for the cytosine and thymidine nucleotides: electrophoretic fractionation of the products of these two reactions gives for all the bases a spot in one or other of the gel columns used. This procedure facilitates the reading of the autoradiogram of the gel. The reaction with hydrazine in the presence of sodium chloride specific for cytosine enables this nucleotide to be distinguished from thymidine and the reaction with dimethyl sulfate followed by cleavage by piperidine, specific for guanine, enables the latter nucleotide to be distinguished from adenine.

In order to ensure the greatest possible degree of accuracy, distinct sequences of nucleotides forming different mutually straddling fragments were produced by hydrolysis of Eco HBV DNA by various restriction enzymes:

BamHi, HinfI, HpaII, HaeIII and HincII.

In this way the analysis of each of the restriction sites used as starting points of the first fragments studied was confirmed by analysis of the separate fragments in which the restriction sites of the first fragments are comprised between the new ends of these separate fragments.

The "gene S" shown in FIGS. 3A, 3B, 3C, which commence by the initiation codon ATG, comprises 227 triplets, including a stop codon TAA. The three codons corresponding to the 3 amino acids of the terminal carboxy end of the corresponding polypeptide are situated in the same reading frame, immediately before the stop codon TAA. One of the two other reading frames (respectively offset to the preceding one by 1 and 2 nucleotides) is also devoid of a stop codon, but codes quite a different protein from the polypeptides I and II above-mentioned. The third reading frame comprises 10 stop codons (5 TAG, 4TGA, 1TAA). On the other DNA strand, the three reading frames are respectively closed by 11, 11, and 6 stop codons distributed along the DNA sequence.

As has already been indicated above, the complete translation of the genetic information starting by the initiation codon ATG leads to a theoretical polypeptide of 226 amino-acids corresponding to a molecular weight of 25,422 daltons.

It is interesting to stress that the nucleotide sequence corresponding to the "gene S" should normally be read entirely in the course of translation.

Equally to be regarded as part of the invention are the nucleotide chains of the above-described "gene S" type, which comprises small additional sequences which can contain up to one hundred nucleotides or which on the contrary may be devoid thereof, without however the corresponding genetic information being altered (22, 23).

The various fragments of the invention which have been defined above may be obtained from the so-called Eco HBV DNA DNA sequence, by resorting to the corresponding restriction enzymes and to the known fractionation techniques of DNA fragments, notably on a polyacrylamide gel and applying their migrations over distances which are a function of their molecular weights. Thus it is possible for example to obtain the fragment of which one of the ends is bounded by an EcoRI site and the other by an AvaIII site by operating an Eco HBV DNA restriction by the AvaIII enzyme, the desired fragment consisting of the smallest fragment obtained (a single AvaIII site in Eco HBV DNA).

The fragment bounded by the opposite ends EcoRI and HhaI is obtained by hydrolysis of Eco HBV DNA by EcoRI first, then by partial hydrolysis by the restriction enzyme HhaI. Among the restriction products was then recovered that which contains the AvaIII site.

These restriction techniques have obviously only been proposed by way of example, it being well understood that the specialist is himself able to determine the order of treatment with restriction enzymes to isolate, starting notably with Eco HBV DNA, the fragments having useful restriction ends.

Insofar as it may be useful, it is recalled that these restriction operations can be carried out in a 10 mM Tris buffer at pH 7.8; 6 mM $MgCl_2$;6 mM$\beta$-mercaptoethanol, the same medium containing in addition preferably 50 mM of NaCl when EcoRI is used.

As has already been said, the invention relates to the use of the DNA fragments described as a probe enabling diagnosis of the presence in a serum of Dane particles or particles derived from the preceding one, bearing a DNA capable of coding an immunogen protein characteristic of hepatitis B.

The DNA according to the invention can also be incorporated in a vector enabling, on condition that the incorporation has been carried out in phase, the expression of this DNA into a bacterium or other microorganism, or into eucaryotic cells.

B—VECTORS CONTAINING A NUCLEOTIDE SEQUENCE OF HBs ANTIGEN

Construction of a λlac HBs-1 recombinant bacteriophage

The products at the level of the different stages of this construction are indicated in FIGS. 1a and 1h. They are also indicated by the numbers 1a to 1h.

In FIG. 1a are indicated the positions of the "gene S" and of certain restriction enzyme sites.

After treatment of DNA+HBV with HhaI restriction enzyme, a DNA fragment (1b) was separated containing 1,084 pairs of bases, and more particularly the whole of the "gene S" by electrophoresis on agarose gel and electroelution (FIG. 1b). There was prepared from this sub-fragment, treated previously by endonuclease S1, a sub-fragment (1c) (FIG. 1c), resulting from the elongation of the sub-fragment (1b) at its ends, by DNA elements named "EcoRI linkers" of the formula:

5' GGAATTCC

CCTTAAGG 3'

The fragment obtained was, after formation of the EcoRI cohesive ends, cloned in the plasmid pBR322.

The plasmid obtained named below pBRHBs (FIG. 1d), only contains a single restriction site XbaI located close to the head of the "gene S".

By digestion of the pBRHBs recombinant plasmid with a mixture of EcoRI and XbaI enzymes, a DNA fragment comprising approximately 980 pairs of bases and including the major part of the "gene S" (FIG. 1e) was produced. This fragment was separated and purified by electrophoresis on agarose gel. The fragment obtained was again treated with S1 endonuclease, then again provided with EcoRI ends by means of the abovesaid "EcoRI linkers" then subjected to treatment with EcoRI endonuclease to reform the corresponding cohesive ends. The fragment of FIG. 1e which comprises about 980 pairs of bases is then inserted by in vitro fusion into the EcoRI site of the plasmid pBR322, to form the plasmid pXbaHBs (FIG. 1f). This plasmid was cloned in the usual manner like the plasmid pBR322.

Several clones were obtained.

There were extracted and purified, after treatment with EcoRI in DNA's of three of these clones, pXbaHBs-1, pXbaHBs-2, pXbaHBs-3 (FIG. 1g), the fragments called below "HBs fragments" (FIG. 1h).

The nucleotide sequences of the ends of the abovesaid fragments (normally obtained inside the "gene S") were determined by resorting to the procedure described by MAXAM and GILBERT (Proc. Nat. Acad. Sci. USA 74, 560–564 (1977). These determinations have shown that the sequences of the nucleotides of the terminal ends, corresponding to the "gene S" were not identical in the three clones (FIG. 1g), the differences are apparently due to heterogeneities produced in the course of digestion with the S1 endonuclease.

The two fragments coming from the pXbaHBs-1 and pXbaHBs-2 were inserted by fusion in vitro into the bacteriophage genome λplac 5-1 (21), which had only a single EcoRI site situated close to the end of the lac Z gene. Due to the fact of the reading frame of the lac Z gene, such as can be produced from the amino-acid sequence of β-galactosidase (23), it is observed—and experiment confirms it—that the insertion of the HBs fragment of pXbaHBs-1 into the EcoRI site of the lac Z gene of λplac 5-1 must lead to the preservation of the adequate reading phase of the "gene S". On the contrary, the insertion of the HBs fragment of pXbaHBs-2 should be revealed as not capable of being inserted into the preceding vector with preservation of the suitable reading frame. It has nonetheless been used as a control in later experiments.

These operations were carried out by resorting to known techniques. In particular the "HBs fragments" of pXbaHBs-1, pXbaHBs-2 were inserted by means of a ligase into the DNA of λplac 5-1 which had previously been cleaved by EcoRI. The mixtures of DNA fragments obtained where then used to transfect the strain C600RecBC rk⁻mk⁻ of E. coli. The bacteriophage clones become lac⁻ due to the fact of the insertion of the HBs fragments into the EcoRI sites of the lac Z gene were amplified and purified by the method described in (21).

The DNA's of the different bacteriophages were extracted and the orientations of the DNA fragments inserted determined by electrophoretic analysis of their BamHI restriction fragments. It was thus possible to determine that two phages called lacHBs-1 and lacHBs-2 corresponding to the pXbaHBs-1 and pXbaHBs-2 plasmid contained a correctly oriented HBs fragment.

FIG. 2a is a diagrammatic chart of the plac 5-1 vector before its modification by the HBs-1 fragment, coming from the pXbaHBs-1.

FIG. 2c is a diagrammatic chart of a portion iw this same vector showing the modification introduced into its gene Z by insertion into its EcoRI site of the abovesaid HBs-1 fragment.

FIG. 2c shows diagrammatically the structures of the hybrid polypeptide obtained as a result of the expression of the modified vector of FIG. 2b.

The expression was achieved by a transfection of a strain of E. coli bacteria, notably of HfrΔlacX74.

The strains of E. coli, notably a strain of E. coli Hfr lac X74 were converted by plac 5-1 and λlacHBs-1 and λlac HBs-2 respectively. After cultivation, the cells were lysed and the lysates obtained analysed by electrophoresis on SDS polyacrylamide gel (24) and the proteins were detected by dyeing with coomassie blue. The presence of a stronger band among the expression products of λplac 5-1 was detected at the level of the position corresponding, for a control, with that of βgalactosidase (molecular weight of 116 248) and of a separate band among the expression products of λlacHBs-1 (not present among the expression products of λlacHBs-2) corresponding to a novel protein having a molecular weight of the order of lac HBs-2) 135 000-141 000.

The proteins synthesized by the bacteria transfected both by λlacHBs-1 and by λplac 5-1 were labelled by (³⁵S) methionine. The contacting of these proteins with an anti-HBsAg serum and the production of an autoradiogram of the SDS polyacrylamide gel reveal the presence among the expression products of only λlacHBs-1 of a band to which there does not correspond an equivalent band among the expression products of the other vectors. This band disappeared specifically when immunoprecipitation was carried out in the presence of unlabelled HBsAg. There was also observed the same band among the λlacHBs-1 expression products, when immunoprecipitation was carried out with an antiserum with respect to β-galactosidase.

The presumed structure of the hybrid protein part obtained, at the level of fusion between the lac Z gene and the HBs-1 fragment results from FIG. 2c which shows the β-gal" fragment, corresponding to β-galactosidase (1,005 amino acids), the HBsAg fragment (192 amino acids), these fragments being separated by a prolyn amino acid, corresponding to a part of "EcoRI linker" contained in the λlacHBs-1 vector.

C—PROCESS FOR MANUFACTURE OF AN IMMUNOGEN MOLECULE APPLYING THE VECTOR ACCORDING TO THE INVENTION

The invention can consequently permit the production of a protein of a molecular weight lower than the aboveindicated polypeptides I or II, endowed with the same immunogen properties.

The results show that E. coli, or any other suitable micro-organism, such as a bacterium or a eucaryotic cell culture, can be infected by λlacHBs-1 and synthesize a protein having a molecular weight of the order of 138,000 and possessing determinants antigenic both of HBsAg and of β-galactosidase. This molecule is representative of the hybrid polypeptides which can be obtained by the process according to the invention, in which HBsAg is connected to a support protein (resulting from the partial or total substitution of the β-galactosidase fragment), these hybrids possessing nonetheless the antigen properties of HBsAg. These novel molecules are useful for the production of vaccines active against viral hepatitis B.

As is self-evident, and as emerges already from the foregoing, the invention is in no way limited to those of its types of application and embodiments which have been more especially envisaged; it encompasses, on the contrary, all modifications.

Appended to this description is a bibliography, in particular of the references which have been cited within the scope of the present description.

REFERENCES

1—Blumberg, B. S. (1977) Science 197, 17-25
2—Dane D. S., Cameron C. H., and Brigss M. (1970) Lancet 1, 695-698
3—Who Technical Report series, number 602 (1976)
4—Summers J., O'Connel A., and Millman I. (1975) Proc. Nat. Acad. Sci. USA 72, 4 597-4 601
5—Hruska J. F., Clayton E. A., Rubenstein J. L. R. and Robinson W. S. (1977) J. Virol. 21, 666-682
6—Landers T. A., Greenberg H. B. and Robinson W. S. (1977) J. Virol. 23, 368-376
7—Charnay P., Pourcel C., Louise A., Fritsch A. and Tiollais P. (1979) Proc. Nat. Acad. Sci. USA, 76 2,222-2,226
8—Dreesman G. R., Hollinger F. B., Surians J. R., Fujioka R. B., Brunschwig J. P. and Melnick J. L. (1972) J. Virol. 10, 469-476
9—Gerin J. L. (1974) in Mechanisms of virus disease Ed. W. S. Robinson, C. R. Fox pp 215-24 Menlo Park: W. A. Benjamin
10—Dreesman G. R., Chairez R., Suarez M., Hollinger F. B. Courtney R. J. and Melnick J. L. (1975) J. Virol. 16, 508-515
11—Shih J. W. and Gerin J. L. (1977) J. Virol. 21, 1,219-1,222
12—Peterson D. L., Roberts I. M. and Vyas G. N. (1977) Proc. Nat. Acad. Sci. USA 74, 1,530-1,534
13—Peterson D. L., Chien D. Y., Vyas G. N., Nitecki D. and Bond H. (1978) in Viral Hepatitis, Ed. G. Vyas, S. Cohen and R. Schmid, The Franklin Institute Press, Philadelphia, 569-573
14—Fritsch A., Pourcel C., Charnay P. and Tiollais P. (1978) C. R. Acad. Sc. Paris 287, 1,453-1,456
15—Burrell C. J., Mackay P., Greenaway P. J., Hofschneider P. H. and Murray K. (1979) Nature 279 43-47
16—Tiollais P., Perricaudet M., Pettersson U. and Philipson L. (1976) Gène i, 49-63
17—Hérissé J., Courtois G., and Galibert F. (1978) Gène 4, 279-294
18—Kroeker W. D. and Laskowski M. S. R. (1977) Anal. Biochem. 79, 63-72
19—Maxam A. M. and Gilbert W. (1977) Proc. Nat. Acad. Sci. USA 74, 560-564
20—Sanger F., Nicklen S. and Coulson A. R. (1977) Proc. Nat. Acad. Sci. USA 74, 5 463-5 467
21—Maat J. and Smith A. J. W. (1978) Nucleic Acid. Res. 5, 4,537-4,545
22—Berget S. M., Moore C. and Sharp P. A. (1977) Proc. Nat. Acad. Sci. USA 74, 3,171-3,175
23—Chow L. T., Gelinas R. E., Broker T. R., and Roberts J. (1977), Cell 12, 1-8
24—Shiraishi H., Kohama T., Shirachi R. and Ishida N. (1977) J. Gen. Virol. 36, 207-210
25—Struck D. K., Lennarz W. J., and Brew K. (1978) J. Biol. Chem. 253, 5,786-5,794
26—Reddy V. B., Thimmappaya B., Dhar R., Subramanian K. N., Zain B. S., Pan J., Celma C. L. and Weissman S. M. (1978) Science 200, 494-502
27—Fiers W., Contreras R., Hargeman G., Rogiers R., Van de Voorde A., Van Henverswyn H., Van Herreweghe J., Volchaerts G. and Ysebaert M. (1978) Nature 273, 113-117
28—Sanger F., Air G. M., Barrell B. G., Brown N. L., Coulson A. R., Fiddes J. C., Hutchison III C. A., Slocombe P. M. and Smith M. (1977) Nature 265, 687-691
29—Barrell B. G., Shaw D. C., Walker J. E., Northrop F. D., Godson G. N. and Fiddes J. C. (1978) Biochem. Soc. Trans. 6, 63-67
30—Szmuness W., Am. J. Path. 81, 629-649 (1975)
31—Sninsky J. J., Siddiqui A., Robinson W. S. and Cohen S. N., Nature 279, 346-348 (1979)
32—Valenzuela P. et al., Nature 280, 815-819 (1979)
33—Charnay P. et al., Nucl. Acids Res. 7, 335-346 (1979)
34—Galibert F., Mandart E., Fitoussi F., Tiollais P. and Charnay P., Nature 281, 646-650 (1979)
35—Pasek M. et al., Nature 282, 575-579 (1979)
36—Vyas G. N., Williams E. W., Klaus G. G. B. and Bond. H. J. Immunol. 108, 1,114-1,118 (1972)
37—Hollinger F. B., Dreesman G. R., Sanchez Y., Cabral G. and Melnick J. L., in Viral Hepatitis (Ed. Vyas G. N. Cohen S. N. and Schmid R.) Franklin Institute, Philadelphia, (1978)
38—Purcell R. H., and Gerin J. L., Am. J. Med. Sci. 270, 395-399 (1975)
39—Hilleman M. R. et al., Am. J. Med. Sci. 270, 401-404 (1975)
40—Maupas P., Coursaget P., Goudeau A. and Drucker J., Lancet 1, 1,367-1,370 (1976)
41—Emtage J. S. et al., Nature 283, 171-174 (1980)
42—Itakura K. et al., Science 198, 1,056-1,063 (1977)
43—Goeddel D. V. et al., Prox. Nat. Acad. Sci. USA 76, 106-110 (1979)
44—Pourcel C., Marchal C., Louise A., Fritsch A. and Tiollais P., Molec. Gen. Genet. 170, 161-169 (1979)
45—Bolivar F. et al., Gene 2, 95-113 (1977)
46—Fowler A. V. and Zabin I., Proc. Nat. Acad. Sci. USA 74, 1,507-1,510 (1977)
47—Laemmli U. K., Nature 227, 680-685 (1970)
48—Burgess R. R., J. Biol. Chem. 244, 6,168-6,176 (1969)
49—Bonner W. M. and Laskey R. A., Eur. J. Biochem. 46, 83-88 (1974)
50—Laskey R. A. and Mills A. D., Eur. J. Biochem. 56, 335-341 (1975)
51—Iwakura Y., Ito K. and Ishihama A., Molec. Gen. Genet. 133, 1-23 (1974)
52—Talwai G. P., et al., Proc. Nat. Acad. Sci. USA 73, 218-222 (1976)

We claim:

1. A peptide which comprises the sequence: Alanine-Glutamine-Glycine-Threonine-Serine, wherein the alanine end is N-terminal and the serine end is C-terminal.

2. A peptide which comprises the sequence: Threonine-Alanine-Glutamine-Glycine-Threonine-Serine, wherein the threonine end is N-terminal and the serine end is C-terminal.

3. A peptide which comprises the sequence: Threonine-Threonine-Alanine-Glutamine-Glycine-Threonine-Serine, wherein the threonine end is N-terminal and the serine end is C-terminal.

4. A peptide which comprises the amino acid sequence of FIG. 5 starting with serine (number 113) and ending with tryptophan (number 165).

5. The peptide of claim 4 which comprises within the peptide the amino acid sequence:
Alanine-Glutamine-Glycine-Threonine-Serine.

6. The peptide of claim 3 which comprises within the peptide the amino acid sequence:
Threonine-Alanine-Glutamine-Glycine-Threonine-Serine.

7. The peptide of claim 4 which comprises within the peptide the amino acid sequence:
Threonine-Threonine-Alanine-Glutamine-Glycine-Threonine-Serine.

8. An immunogenic peptide sequence which comprises the amino acids shown in FIGS. 3A, 3B, and 3C numbering not less than 5 amino acids and not more than 226 amino acids which peptide induces in vivo the production of active antibodies with respect to the hepatitis B virus.

9. The immunogenic peptide sequence which comprises the amino acids shown in FIG. 6 numbering not less than 5 amino acids and not more than 53 amino acids, which peptide induces in vivo the production of active antibodies with respect to the hepatitis B virus.

10. A pharmaceutical composition comprising an effective amount of the peptides of claims 1, 2, 3, 4, 5, 6 or 7, wherein composition induces in vivo production of antibodies, the hepatitus B-viruis, and a pharmaceutically acceptable carrier.

* * * * *

UNITED STATES PATENT AND TRADEMARK OFFICE
CERTIFICATE OF CORRECTION

PATENT NO. :  4,428,941

DATED       :  Jan. 31, 1984

INVENTOR(S) :  Galibert et al

It is certified that error appears in the above—identified patent and that said Letters Patent is hereby corrected as shown below:

On the information page under item (30), Foreign Application Priority Date, the filing date for French application ser. no. 79 21811 shown as "August 3, 1979" should read --August 30, 1979--.

Signed and Sealed this

Seventeenth Day of February, 1987

Attest:

DONALD J. QUIGG

Attesting Officer

Commissioner of Patents and Trademarks